(12) United States Patent
Hwang

(10) Patent No.: US 10,961,276 B2
(45) Date of Patent: Mar. 30, 2021

(54) UNIVERSAL ANTIVENOM

(71) Applicant: CAMRIS International, Inc., Bethesda, MD (US)

(72) Inventor: Yoon Y. Hwang, San Antonio, TX (US)

(73) Assignee: CAMRIS International, Inc., Bethesda, MD (US)

( * ) Notice: Subject to any disclaimer, the term of this patent is extended or adjusted under 35 U.S.C. 154(b) by 0 days.

(21) Appl. No.: 16/486,639

(22) PCT Filed: Feb. 16, 2018

(86) PCT No.: PCT/US2018/000084
§ 371 (c)(1),
(2) Date: Aug. 16, 2019

(87) PCT Pub. No.: WO2018/151867
PCT Pub. Date: Aug. 23, 2018

(65) Prior Publication Data
US 2019/0382449 A1    Dec. 19, 2019

Related U.S. Application Data

(60) Provisional application No. 62/460,213, filed on Feb. 17, 2017.

(51) Int. Cl.
*C07K 7/64* (2006.01)
*C12N 15/73* (2006.01)
*A61K 38/08* (2019.01)
*A61K 38/00* (2006.01)

(52) U.S. Cl.
CPC ............. *C07K 7/64* (2013.01); *A61K 38/08* (2013.01); *C12N 15/73* (2013.01); *A61K 38/00* (2013.01); *C12N 2795/14121* (2013.01); *C12N 2795/14131* (2013.01)

(58) Field of Classification Search
None
See application file for complete search history.

(56) References Cited

PUBLICATIONS

Prado et al., PLoS One. Mar. 30, 2016;11(3):e0151363 (Year: 2016).*
Lausten (Recombinant Antivenoms. PhD thesis, University of Copenhagen, 2016) (Year: 2016).*

* cited by examiner

*Primary Examiner* — Sergio Coffa
(74) *Attorney, Agent, or Firm* — Sterne, Kessler, Goldstein & Fox P.L.L.C.

(57) ABSTRACT

The present disclosure is directed to a universal antivenom for the treatment of venomous animal bites, and methods of developing the same using a novel targeted phage display technique.

9 Claims, 6 Drawing Sheets
Specification includes a Sequence Listing.

MSLFQFEKLIKKMTGKSGMLWYSAYGCYCGWGGXGRPXDATDRCCFYHDCCYGKVTGCNPKMDIYTYSVENGNIVCGGTNPCKKQICECDRAAAICFRDNLLTYDSKTYWKYPKNCTKEE

FIG. 1B

PLA₂ Activity inhibition of Western Cottonmouth venom after incubation with polyclonal phage mixture

SEQUENCE LISTING

<160> NUMBER OF SEQ ID NOS: 16

<210> SEQ ID NO 1
<211> LENGTH: 7
<212> TYPE: PRT
<213> ORGANISM: Artificial Sequence
<220> FEATURE:
<223> OTHER INFORMATION: Ph.D.-C7C-6

<400> SEQUENCE: 1

```
Ser Pro Leu His Lys Thr Met
1               5

<210> SEQ ID NO 2
<211> LENGTH: 7
<212> TYPE: PRT
<213> ORGANISM: Artificial Sequence
<220> FEATURE:
<223> OTHER INFORMATION: Ph.D.-C7C-7

<400> SEQUENCE: 2

Ser Gly Met Lys Lys Thr Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Ph.D.-C7C-9

<400> SEQUENCE: 3

Lys Thr Thr Lys Met Gly Leu
1               5

<210> SEQ ID NO 4
<211> LENGTH: 12
<212> TYPE: PRT
<213> ORGANISM: Artificial Sequence
<220> FEATURE:
<223> OTHER INFORMATION: Ph.D.-12-2

<400> SEQUENCE: 4

Lys Leu Ile His Gly Asn Gly Val Met Asp Glu Gly
1               5                   10

<210> SEQ ID NO 5
<211> LENGTH: 21
<212> TYPE: DNA
<213> ORGANISM: Artificial Sequence
<220> FEATURE:
<223> OTHER INFORMATION: Ph.D.-C7C-6

<400> SEQUENCE: 5
tcgccgttgc ataagactat g                                          21

<210> SEQ ID NO 6
<211> LENGTH: 21
<212> TYPE: DNA
<213> ORGANISM: Artificial Sequence
<220> FEATURE:
<223> OTHER INFORMATION: Ph.D.-C7C-7

<400> SEQUENCE: 6
tcggggatga agaagacgaa g                                          21

<210> SEQ ID NO 7
<211> LENGTH: 21
<212> TYPE: DNA
<213> ORGANISM: Artificial Sequence
<220> FEATURE:
<223> OTHER INFORMATION: Ph.D.-C7C-9

<400> SEQUENCE: 7
aagacgacga agatggggtt g                                          21
```

```
<210> SEQ ID NO 8
<211> LENGTH: 36
<212> TYPE: DNA
<213> ORGANISM: Artificial Sequence
<220> FEATURE:
<223> OTHER INFORMATION: Ph.D.-12.-7

<400> SEQUENCE: 8
aagcttattc atggtaatgg tgttatggat gagggg                              36

<210> SEQ ID NO 9
<211> LENGTH: 7
<212> TYPE: PRT
<213> ORGANISM: Artificial Sequence
<220> FEATURE:
<223> OTHER INFORMATION: Inverse of Ph.D.-C7C-6

<400> SEQUENCE: 9

Met Thr Lys His Leu Pro Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Inverse of Ph.D.-C7C-7

<400> SEQUENCE: 10

Lys Thr Lys Lys Met Gly Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Inverse of Ph.D.-C7C-9

<400> SEQUENCE: 11

Leu Gly Met Lys Thr Thr Lys
1               5

<210> SEQ ID NO 12
<211> LENGTH: 12
<212> TYPE: PRT
<213> ORGANISM: Artificial Sequence
<220> FEATURE:
<223> OTHER INFORMATION: Ph.D.-12-2

<400> SEQUENCE: 12

Gly Glu Asp Met Val Gly Asn Gly His Ile Leu Lys
1               5                   10

<210> SEQ ID NO 13
<211> LENGTH: 21
<212> TYPE: DNA
<213> ORGANISM: Artificial Sequence
<220> FEATURE:
<223> OTHER INFORMATION: Inverse of Ph.D.-C7C-6

<400> SEQUENCE: 13
atgaccaaac atctgccgag c                                              21

<210> SEQ ID NO 14
<211> LENGTH: 21
<212> TYPE: DNA
```

```
<213> ORGANISM: Artificial Sequence
<220> FEATURE:
<223> OTHER INFORMATION: Inverse of Ph.D.-C7C-7

<400> SEQUENCE: 14
aaaaccaaaa aaatgggcag c                                              21

<210> SEQ ID NO 15
<211> LENGTH: 21
<212> TYPE: DNA
<213> ORGANISM: Artificial Sequence
<220> FEATURE:
<223> OTHER INFORMATION: Inverse of Ph.D.-C7C-9

<400> SEQUENCE: 15
ctgggcatga aaaccaccaa a                                              21

<210> SEQ ID NO 16
<211> LENGTH: 36
<212> TYPE: DNA
<213> ORGANISM: Artificial Sequence
<220> FEATURE:
<223> OTHER INFORMATION: Inverse of Ph.D.-12.-7

<400> SEQUENCE: 16
ggcgaagata tggtgggcaa cggccatatt ctgaaa                              36
```

UNIVERSAL ANTIVENOM

CROSS-REFERENCE TO RELATED APPLICATIONS

This application claims the benefit of U.S. Provisional Application No. 62/460,213, filed Feb. 17, 2017, the entire contents of which are herein incorporated by reference.

STATEMENT REGARDING FEDERALLY SPONSORED RESEARCH

This invention was made with government support under ILIR-5160 awarded by the Navy In-House Laboratory Independent Research Program. The government has certain rights in the invention.

REFERENCE TO SEQUENCE LISTING SUBMITTED ELECTRONICALLY

The content of the electronically submitted sequence listing (Name: 4133.001PC01_ST25.txt; Size: 32,474 bytes; and Date of Creation: Feb. 15, 2018) is herein incorporated by reference in its entirety.

FIELD OF THE DISCLOSURE

The present disclosure relates generally to development of universal antivenom using phages displaying short peptides.

BACKGROUND

M13 phages expressing short peptides have been utilized as delivery vehicles to transport various binding motifs to targets. Genetic modification to phage tail proteins allows for the expression of unique peptides of variable sequences, length, and composition. Expressed peptides can bind to specific epitopes, forming the basis of a high throughput system for identifying binding partners.

Animal envenomation is a major public health concern worldwide and is classified as a neglected disease by the World Health Organization. For instance, approximately 400,000 people worldwide, with nearly 9,000 in the United States and Canada, are affected every year by snakebite envenomation. Several antibody-based antivenoms are available for envenomation treatment. Crotalidae polyvalent immune Fab (Ovine) is currently the only widely available product for the treatment of patients with North American crotalid; however its high cost and side effects are common concerns.

Antibody-based antivenoms are developed by exposing host animals to pure venom for immunological conditioning, and extracting the resulting antibodies. While an antibody-based strategy has yielded successful therapies for some snake species, there remain limitations in safety, efficacy, and cost of manufacturing. Additionally, antibody-based strategies have limited effectiveness in combating envenomation from other animals such as arachnids and medusae.

Serum is then isolated from the animals, and venom-reactive antibodies purified. While this antibody-based strategy has yielded successful therapies for some snake species, there remain limitations in safety, efficacy, and the economic aspects of manufacturing. One of the most serious side effects of antibody-based antivenom is patient's immunological reactions against heterologous immunoglobulins from horses or sheep, known as serum sickness. In addition, most antibody-based solutions require either special storage conditions or, if lyophilized, reconstitution prior to administration; both of which diminish their utility in remote and austere conditions. Although others have produced antibody-based antivenoms, their continued pursuit of antivenom production is questionable given the impact of a costly and time-consuming production process, as well as limitations of application.

The following references provide background information on the state of the art in antivenom technology and are herein incorporated by reference in their entireties: Molenaar, T. J. et al. Uptake and processing of modified bacteriophage M13 in mice: implications for phage display. *Virology* 293, 182-191, doi:10.1006/viro.2001.1254 (2002); Rabies and Envenomings A Neglected Public Health Issue (WHO 2007); WHO Guidelines for the Production Control and Regulation of Snake Antivenom Immunoglobulins (WHO 2010); Warrell, D. A. Guidelines for the management of snake-bites (WHO 201 0); Smith, S. et al. Bedside management considerations in the treatment of pit viper envenomation. *J Emerg Nurs* 40, 537-545, doi:10.1016/j.jen.2014.01.002 (2014); Mowry, J. B., Spyker, D. A., Cantilena, L. R., Jr., Bailey, J. E. & Ford, M. 2012 Annual Report of the American Association of Poison Control Centers' National Poison Data System (NPDS): 30th Annual Report. Clin Toxicol (Phila) 51, 949-1229, doi:10.3109/15563650.2013.863906 (2013); Kanaan, N.C. et al. Wilderness Medical Society Practice Guidelines for the Treatment of Pitviper Envenomations in the United States and Canada. *Wilderness Environ Med* 26, 472-487, doi:10.1016/j.wem.2015.05.007 (2015); Holland, D. R. et al. The crystal structure of a lysine 49 phospholipase A2 from the venom of the cottonmouth snake at 2.0-A resolution. *J Biol Chem* 265, 17649-17656 (1990); Fralick, J., Chadha-Mohanty, P. & Li, G. in Advances in Biological and Chemical Terrorism Countermeasures (eds R. Kendall, S. Presley, G. Austin, & P. Smith) 179-202 (CRC Press, 2008); Philipson, L., Albertsson, P. A., Frick, G. The purification and concentration of viruses by aqueous polymer phase systems. *Virology*, 11, 553-571 (1960); Yu, J. & Smith, G. P. [1] Affinity maturation of phage-displayed peptide ligands. 267, 3-27, doi: 10.1016/s0076-6879(96)67003-7 (1996); Prakash S.S. Phage display technology for anti-venom production. Clinical Microbiology and Infection 13:4 (October 2015); Roncolato, E. C. et al. Phage display as a novel promising antivenom therapy: a review. 93:79-84 Toxicon. (January 2015; Epub November 2014).

SUMMARY

The present disclosure provides a multi-species antivenom composition. The composition contains phage-expressed peptides that bind to a target common to several different animal venoms. The phage-expressed peptide is typically a 7-12 mer peptide that can bind to many targets, including metals, carbohydrates, and proteins.

The present disclosure also provides an improved method of peptide target design based on compiling a consensus protein sequence reflecting a plurality of animal venoms. The consensus protein sequence then provides a target for phage display panning (affinity partitioning for the enrichment homologous regions of different venom protein sequences).

In an exemplary embodiment, the present disclosure provides an improved method of peptide target design based on the consensus Phospholipases $A_2$ ($PLA_2$) protein sequence in Western Cottonmouth venom. This consensus sequence thus provides a target for phage display panning in the generation of an antivenom universal to North American venomous snakes. The method comprises redefining the target sequence to include homologous regions of the seven most common venomous snakes in North America. Specifically, this method involves redefining the target peptide to mimic homologous regions of peptide families through targeting conserved active sites. This method can use a phage-expressed peptide listed in Table 1, below.

The present disclosure also relates to an antivenom formulation that includes a phage-expressed peptide, suspended in a pharmaceutically acceptable carrier, wherein the peptide is configured to bind to conserved snake venom components, and thereby neutralize venom toxicity.

The present disclosure also provides a diagnostic kit for identifying the type and severity of a venomous animal bite. The kit contains a plurality of peptides, and a plurality of label molecules. Each peptide targets a sequence unique to the venom of one or more animal species. Each label molecule is conjugated to a corresponding unique peptide. A bite victim's blood is drawn and contacted with the peptide/label conjugates. The kit also includes an assay configured to detect the label molecules and thereby display the peptides that are bound to their respective targets in the blood. The kit can therefore detect which peptides have bound to targets, and the extent of the binding, thereby identifying what animal species venom is found in the blood and the severity of the bite.

In some embodiments, disclosed herein is a multi-species antivenom composition comprising a phage-expressed peptide that binds to a target common to venom of more than one animal and a pharmaceutically acceptable carrier. In some embodiments, the phage-expressed peptide is about 7 to about 12 amino acids in length; and wherein the target is a metal, a carbohydrate, a protein, or any combination thereof. In some embodiments, the phage-expressed peptide is linear. In some embodiments, the phage-expressed peptide is circular.

In some embodiments, the target of the phage-expressed peptide is a protein. In some embodiments, the target of the phage-expressed peptide is phospholipase $A_2$ ($PLA_2$).

In some embodiments, the composition comprises one or more peptides selected from the group consisting of SEQ ID NO:1, SEQ ID NO:2, SEQ ID NO:3, SEQ ID NO:4, and any combination thereof. In some embodiments, the composition comprises a peptide comprising SEQ ID NO:1. In some embodiments, the composition comprises a peptide consisting of SEQ ID NO:1. In some embodiments, the composition comprises a peptide comprising SEQ ID NO:2. In some embodiments, the composition comprises a peptide consisting of SEQ ID NO:2. In some embodiments, the composition comprises a peptide comprising SEQ ID NO:3. In some embodiments, the composition comprises a peptide consisting of SEQ ID NO:3. In some embodiments, the composition comprises a peptide comprising SEQ ID NO:4. In some embodiments, the composition comprises a peptide consisting of SEQ ID NO:4.

In some embodiments, the composition comprises one or more peptides selected from the group consisting of SEQ ID NO: 9, SEQ ID NO:10, SEQ ID NO:11, SEQ ID NO:12, and any combination thereof. In some embodiments, the composition comprises a peptide comprising SEQ ID NO:9. In some embodiments, the composition comprises a peptide consisting of SEQ ID NO:9. In some embodiments, the composition comprises a peptide comprising SEQ ID NO:10. In some embodiments, the composition comprises a peptide consisting of SEQ ID NO:10. In some embodiments, the composition comprises a peptide comprising SEQ ID NO:11. In some embodiments, the composition comprises a peptide consisting of SEQ ID NO:11. In some embodiments, the composition comprises a peptide comprising SEQ ID NO:12. In some embodiments, the composition comprises a peptide consisting of SEQ ID NO:12.

In some embodiments, disclosed herein are compositions comprising a phage expressed peptide, wherein the phage-expressed peptide is expressed by a M13 phage.

In some embodiments, disclosed herein are compositions that neutralize a plurality of animal venoms, wherein the plurality of animal venoms originates from one or more species of snakes.

In some embodiments, disclosed herein are one or more phage-expressed peptides that bind to a target in one or more animal venoms. In some embodiments, the phage-expressed peptides are selected from the group consisting of SEQ ID NO:1, SEQ ID NO:2, SEQ ID NO:3, SEQ ID NO:4, and any combination thereof. In some embodiments, the phage expressed peptide targets phospholipase $A_2$. Still in some embodiments, the one or more phage expressed peptides comprise peptides selected from the group consisting of SEQ ID NO: 9, SEQ ID NO:10, SEQ ID NO:11, SEQ ID NO:12, and any combination thereof. In some embodiments, the phage-expressed peptide is expressed by a M13 phage.

Also provided herein are one or more isolated nucleic acid molecules encoding any one of the peptides disclosed herein. In some embodiments, the nucleic acid molecules comprise sequences selected from SEQ ID NO: 5, SEQ ID NO:6, SEQ ID NO:7, SEQ ID NO:8, SEQ ID NO:13, SEQ ID NO:14, SEQ ID NO:15, SEQ ID NO:16, and any combination thereof.

In some embodiments, provided herein are one or more vectors comprising a nucleic acid that encodes for any one of the peptides disclosed herein. In some embodiments, the one or more vectors comprise a nucleic acid disclosed herein.

In some embodiments, provided herein is a host cell comprising an isolated nucleic acid molecule disclosed herein, or the isolated vector disclosed herein. In some embodiments, the host cell is a prokaryote cell. In some embodiments, the host cell is *Escherichia coli*. In some embodiments, the host cell is *Escherichia coli* K12 ER2738.

In some embodiments, also provided herein is a method of producing a composition disclosed herein or a peptide disclosed herein comprising culturing a host cell disclosed herein under conditions where the peptide is produced. In some embodiments, provided herein is a method of producing a composition disclosed herein or the peptide disclosed herein comprising (a) identifying a consensus $PLA_2$ protein sequence in in Western Cottonmouth venom; (b) identifying consensus $PLA_2$ protein sequences in in other snake species; and (c) producing one or more phages via phage display panning.

In some embodiments, disclosed herein is a method of treatment of a subject in contact with animal venom, comprising administering to the subject a composition disclosed herein. In some embodiments, the animal venom is from Western Cottonmouth venom. In some embodiments, the composition binds to the animal venom, thereby neutralizing venom toxicity. In some embodiments, the composition administered comprises a peptide selected from the group consisting of SEQ ID NO:1, SEQ ID NO:2, SEQ ID NO:3, SEQ ID NO:4, SEQ ID NO:9, SEQ ID NO:10, SEQ ID NO:11, SEQ ID NO:12, and any combination thereof. In some embodiments, the composition is administered though oral, rectal, transdermal, intravenous, intramuscular, intraperitoneal, in the bone marrow, epidural, or subcutaneous means.

In some embodiments, provided herein is a diagnostic kit comprising a composition disclosed herein. In some embodiments, the kit comprises a composition comprising peptides selected from SEQ ID NO:1, SEQ ID NO:2, SEQ ID NO:3, SEQ ID NO:4, and any combination thereof. In some embodiments, the kit comprises a composition comprising peptides selected from SEQ ID NO:9, SEQ ID NO:10, SEQ ID NO:11, SEQ ID NO:12, and any combination thereof.

BRIEF DESCRIPTION OF THE DRAWINGS

The following will be apparent from elements of the figures, which are provided for illustrative purposes and are not necessarily to scale.

FIG. 1B is the conserved sequence of PLA$_2$ from Western Cottonmouth snake venom used as the target peptide for panning. The interior region denoting the active catalytic sites (yellow) and the metal binding sites (red) was utilized as the template peptide for phage panning.

FIG. 2 is a graphical representation of PLA$_2$ inhibition when Western Cottonmouth venom is incubated for 30 minutes with the polyclonal phage mixture from the second round of panning. The inhibition effect is dependent on the concentration of the polyclonal phage mixture.

FIG. 5A shows a sequence analysis of venom components. FIG. 5B shows an affinity selection of phages. FIG. 5C shows an in vitro and in vivo efficacy testing. FIG. 5D shows phage treatment for snakebite victims.

Figure 1A:
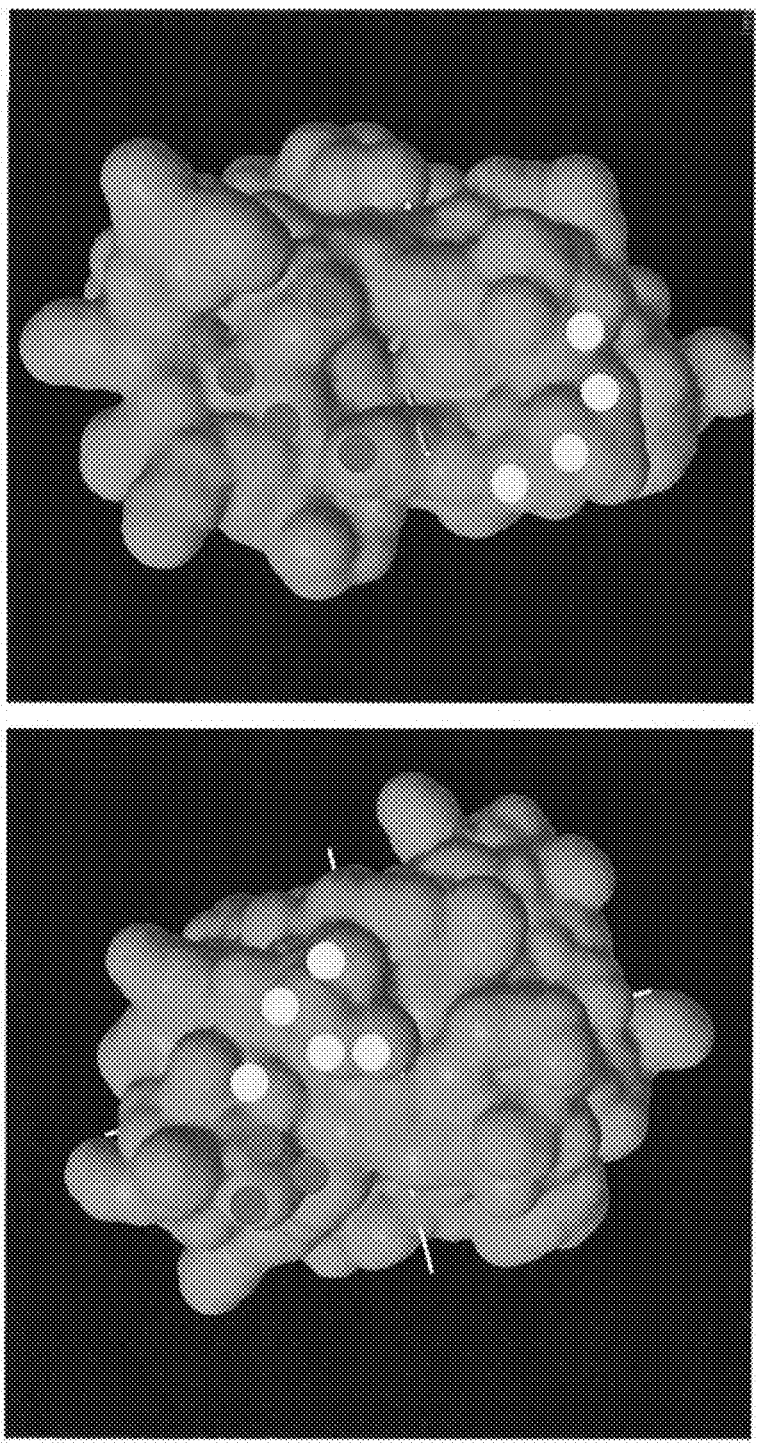
FIG. 1A shows the crystal structure of PLA$_2$ isolated from Western Cottonmouth (*Agldstrodon piscivorus leucostoma*) venom in a space filling model. Residues have been identified using circles, denoting catalytic network, and metal binding amino acids, respectively. The secondary image shows a 90° counter-clockwise rotation of the crystal structure for viewing the active residues.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the disclosure as defined by the appended claims.

DETAILED DESCRIPTION

Provided herein are peptides and compositions comprising peptides. In some embodiments, the peptides bind to snake venom and neutralize venom toxicity. In some embodiments, the peptides bind to PLA$_2$ and neutralize venom toxicity. In a specific embodiment, the proteins disclosed herein are isolated.

Also provided are isolated nucleic acids (polynucleotides), such as complementary DNA (cDNA), encoding such proteins. Further provided are vectors (e.g., expression vectors) and cells (e.g., host cells) comprising nucleic acids (polynucleotides) encoding such proteins. Also provided are methods of making such proteins. In other aspects, provided herein are methods and uses for detecting snake venom. In other aspects, provided herein are methods of treatment of certain conditions, such as a snake bite. Related compositions (e.g., pharmaceutical compositions), kits, and detection methods are also provided.

For the purposes of promoting an understanding of the principles of the disclosure, reference will now be made to a number of illustrative embodiments illustrated in the drawings and specific language will be used to describe the same.

a. Terminology

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "phage" or "bacteriophage" refers to a virus that infects bacteria. The term "phage" is used to refer to both types of viruses but in certain instances as indicated by the context may also be used as shorthand to refer to a bacteriophage specifically. Bacteriophage are obligate intracellular parasites that multiply inside bacteria by making use of some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid may be either DNA or RNA but not both and it can exist in various forms. Phages have two means by which to infect bacterial cells. One is lysogeny, in which the phage DNA incorporates into the chromosome of the bacterium and becomes dormant for many generations. At least one environmental inducer is required to cause the phage DNA to excise from the bacterial chromosome and establish the second type of infection, the lytic phase. In this phase, the bacterium is transformed into a phage-making factory. Hundreds of phages are produced and the bacterial cell is lysed to release them. The released phage then find another host bacterium, and the process repeats.

"M13 phages," "M13 bacteriophage" and the like are bacteriophages that are invected with an M13 virus. In some embodiments disclosed herein, M13 phages are *Escherichia coli* that is infected with an M13 virus. An M13 phage is composed of a circular single-stranded DNA molecule encased by a coating protein. In some embodiments disclosed herein, M13 phages produce antivenom peptides comprising SEQ ID NOs: 1-4.

"Antivenom" is a serum which acts against the effects of venom. Antivenom is used to treat certain venomous bites and stings. In one particular embodiment herein, antivenom is used to treat a snake bite. Specific antivenom needed depends on the species involved. "Universal antivenom reacts with venom or proteins of venom of more than one species. Said another way, Universal antivenom is antivenom that cross-reacts with venoms of different species.

"Phage display panning" is a technique to examine protein-protein, protein-peptide, and protein-DNA interactions using bacteriophages. Phage displace panning allows for enrichment of relevant phage.

"Phospholipidase $A_2$" or "$PLA_2$" is an enzyme that belongs to a class of enzymes hydrolyze the sn-2 ester of glycerophospholipids to produce a fatty acid and a lysophospholipid. $PLA_2$ catalyzes the calcium-dependent hydrolysis of the 2-acyl groups in 3-sn-phosphoglycerides, and this releases glycerophospholipids and arachidonic acid that serve as the precursors of signal molecules. $PLA_2$ of snake venoms comprise a very large superfamily of enzymes composed of 16 recognized groups within six major types. These major types include the secreted $PLA_2$s ($sPLA_2$), the cytosolic $PLA_2$s ($cPLA_2$), the calcium independent $PLA_2$s ($iPLA_2$) the platelet activating factor (PAF) acetyl hydrolase/oxidised lipid lipoprotein associated $PLA_2$($LpPLA_2$s), the adipose $PLA_2$s ($AdPLA_2$s) and the lysosomal $PLA_2$s ($LPLA_2$s). The hydrolysis of glycerophospholipids by $PLA_2$s results in the release of fatty acid and the production of the relevant lysophospholipid.

A "consensus sequence" is a sequence of nucleotides or amino acids in common between regions of homology in different but related DNA or RNA or protein sequences.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination.

As used herein, an "amino acid corresponding to," "site corresponding to," or "equivalent amino acid" in a protein sequence is identified by alignment to maximize the identity or similarity between a first protein sequence, e.g., a IL-2 sequence, and a second protein sequence, e.g., a second IL-2 sequence. The number used to identify an equivalent amino acid in a second protein sequence is based on the number used to identify the corresponding amino acid in the first protein sequence.

The term "expression" as used herein refers to a process by which a polynucleotide produces a gene product, for example, an RNA or a polypeptide.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, a predicted nonessential amino acid residue in IL-2-CD25 fusion protein is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187

(1993); Kobayashi et al. *Protein Eng.* 12(10):879-884 (1999); and Burks et al. *Proc. Natl. Acad. Sci. USA* 94:412-417 (1997)).

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

"Binding affinity" generally refers to the strength of the sum total of non-covalent interactions between a single binding site of a molecule (e.g., an peptide disclosed herein) and its binding partner (e.g., an antigen). Unless indicated otherwise, as used herein, "binding affinity" refers to intrinsic binding affinity which reflects a 1:1 interaction between members of a binding pair (e.g., a peptide and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., a peptide to an antigen, and $k_{off}$ refers to the dissociation of, e.g., a peptide to an antigen. The $k_{on}$ and $k_{off}$ can be determined by techniques known to one of ordinary skill in the art, such as BIAcore® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a peptides disclosed herein can be replaced with an amino acid residue with a similar side chain.

As used herein, an "epitope" is a term in the art and refers to a localized region of an antigen to which a peptide can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an peptide disclosed herein binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303).

The term "nucleic acid molecule," as used herein, is intended to include DNA molecules and RNA molecules. A nucleic acid molecule can be single-stranded or double-stranded, and can be cDNA.

The term "downstream" refers to a nucleotide sequence that is located 3' to a reference nucleotide sequence. "Downstream" can also refer to a peptide sequence that is located C-terminal to a reference peptide sequence.

The term "upstream" refers to a nucleotide sequence that is located 5' to a reference nucleotide sequence. "upstream" can also refer to a peptide sequence that is located N-terminal to a reference peptide sequence.

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide, which encodes a gene product, e.g., a polypeptide, can include a promoter and/or other transcription or translation control elements operably associated with one or more coding regions. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions, which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "percent sequence identity," "percent identity," "sequence identity," or "identity" are used interchangeably and refers to the number of identical matched positions shared between two polynucleotide or polypeptide sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The comparison of sequences and determination of percent identity between two sequences can be accomplished using a mathematical algorithm, as described in the non-limiting examples below.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules described herein. BLAST protein searches can be performed with the XBLAST program, score=50, word length=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein. Exemplary host cells include, but are not limited to, prokaryotic cells (e.g., *E. coli*), or alternatively, eukaryotic cells, for example, fungal cells (e.g., yeast cells such as *Saccharomyces cerevisiae, Pichia pastoris*, or *Schizosaccharomyces pombe*), and various animal cells, such as insect cells (e.g., Sf-9) or mammalian cells (e.g., HEK293F, CHO, COS-7, NIH-3T3).

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which a heterologous moiety (e.g., a half-life extending moiety) is inserted between two adjacent amino acids.

"Treat," "treatment," or "treating," as used herein refers to, e.g., the reduction in severity of a disease or condition; the reduction in the duration of a condition course; the amelioration or elimination of one or more symptoms associated with a disease or condition; the provision of beneficial effects to a subject with a disease or condition, without necessarily curing the disease or condition.

As used herein, "administering" refers to the physical introduction of a composition comprising a therapeutic agent to a subject, using any of the various methods and delivery systems known to those skilled in the art. Different routes of administration for peptides described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, a peptide described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

By "vaccine" is intended a composition useful for stimulating a specific immune response (or immunogenic response) in a subject. In some embodiments, the immunogenic response is protective or provides protective immunity. For example, in the case of a disease-causing organism the vaccine enables the subject to better resist infection with or disease progression from the organism against which the vaccine is directed. Alternatively, in the case of a cancer, the vaccine strengthens the subject's natural defenses against cancers that have already developed. These types of vaccines may also prevent the further growth of existing cancers, prevent the recurrence of treated cancers, and/or eliminate cancer cells not killed by prior treatments.

As used herein, the term "effective amount" in the context of the administration of a therapy to a subject refers to the amount of a therapy that achieves a desired prophylactic or therapeutic effect.

As used herein, the terms "subject" and "patient" are used interchangeably. The subject can be an animal. In some embodiments, the subject is a mammal such as a non-primate (e.g., cow, pig, horse, cat, dog, rat, etc.) or a primate (e.g., monkey or human), most preferably a human. In certain embodiments, such terms refer to a non-human animal (e.g., a non-human animal such as a pig, horse, cow, cat or dog). In some embodiments, such terms refer to a pet or farm animal. In specific embodiments, such terms refer to a human.

As used herein, the terms "ug" and "uM" are used interchangeably with "µg" and "µM," respectively.

Various aspects described herein are described in further detail in the following subsections.

b. Peptides

The present disclosure also identifies phage-expressed peptides which strongly bind to conserved snake venom components, and neutralize venom toxicity. In some embodiments disclosed herein are peptides that strongly bind to conserved snake venom components. In some embodiments, disclosed herein are peptides that neutralize venom toxicity. In some embodiments, disclosed herein are peptides that strongly bind to conserved snake venom components and neutralize venom toxicity.

Unlike, for example, antibody-based antivenom therapies that are confined to antigen targeting, the phage display of the present disclosure offers a powerful tool for the selection of phage-expressed peptides that bind with high specificity and affinity to many different targets. These phage expressed peptides are short, typically 7-12-mer fragments that can be linear or circular in structure. Examples include circular 7-mer and linear 12-mer peptides.

In one embodiment, disclosed herein is a liner 7-mer. In one embodiment, disclosed herein is a liner 8-mer. In one embodiment, disclosed herein is a liner 9-mer. In one embodiment, disclosed herein is a liner 10-mer. In one embodiment, disclosed herein is a liner 11-mer. In one embodiment, disclosed herein is a liner 12-mer.

In one embodiment, disclosed herein is a circular 7-mer. In one embodiment, disclosed herein is a circular 8-mer. In one embodiment, disclosed herein is a circular 9-mer. In one embodiment, disclosed herein is a circular 10-mer. In one embodiment, disclosed herein is a circular 11-mer. In one embodiment, disclosed herein is a circular 12-mer.

Metals, carbohydrates, and proteins are main components of animal venom. Peptides disclosed herein can target many macromolecules. In some embodiments, disclosed herein are peptides that target metals, carbohydrates, and proteins. In some embodiments, disclosed herein are peptides that target metals and carbohydrates. In some embodiments, disclosed herein are peptides that target metals and proteins. In some embodiments, disclosed herein are peptides that target carbohydrates, and proteins. In some embodiments, the peptides disclosed herein target carbohydrates. In some embodiments, disclosed herein are peptides that bind to proteins. In one embodiment, the peptides disclosed herein target metals.

Disclosed herein are peptides comprising a sequence selected from the groups consisting of SEQ ID NOs: 1-4. In one embodiment, disclosed herein is a peptide comprising SEQ ID NO:1 (SPLHK™; also termed Ph.D.-C7C-6). In one embodiment, disclosed herein is a peptide comprising SEQ ID NO:2 (SGMKKTK; also termed Ph.D.-C7C-7). In one embodiment, disclosed herein is a peptide comprising SEQ ID NO:3 (KTTKMGL; also termed Ph.D.-C7C-9). In one embodiment, disclosed herein is a peptide comprising SEQ ID NO:4 (KLIHGNGVMDEG; also termed Ph.D.-12-2 or Ph.D.-12-7).

In some embodiments disclosed herein are biologically active variants of SEQ ID NOs: 1-4. In some embodiments, the biologically active fragments and variants of SEQ ID NOs: 1-4 comprise at least 50%, at least 60%, at least 70%, at least 75%, at least 80%, at least 85%, at least 90%, or at least 95% sequence identity to the sequence set forth in SEQ ID NOs: 1-4.

In some embodiments, the biologically active variants include one or more additional amino acids compared to SEQ ID NOs: 1-4. In some embodiments, the biologically active variants include one or fewer amino acids compared to SEQ ID NOs: 1-4.

In some embodiments, the biological variants of the peptides disclosed herein comprise one or more mutations. In some embodiments, the mutation is a substitution mutation. In some embodiments, the substitution is a conservative substitution of amino acids that do not influence protein folding and or activation. Examples of conservative substitution belong to the group consisting of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activity are known in the art of the present invention. Most common occurred alteration are Ala/Ser, Vai/IIe, Asp/Giu, Thr/Ser, Ala/Giy, Ala/Thr, Ser/Asn, Ala/Val, Ser/Giy, Tyr/Phe, Ala/Pro, Lys/Arg, Asp/Asn, Leu/IIe, Leu/Val, Ala/Giu, Asp/Giy, and the opposite alterations.

In some embodiments, disclosed herein are the inverse consensus peptide sequences of SEQ ID NOs:1-4. In one embodiment, an inverse consensus peptide sequence comprises SEQ ID NO:9. In one embodiment, an inverse consensus peptide sequence comprises SEQ ID NO:10. In one embodiment, an inverse consensus peptide sequence comprises SEQ ID NO:11. In one embodiment, an inverse consensus peptide sequence comprises SEQ ID NO:12.

In another embodiment of the present disclosure, the peptides having the inverse of the consensus sequences of SEQ ID NOs:1-4 are used to develop a bite or sting diagnostic kit. Kits are described in more detail below.

TABLE 1

Peptide Sequences and Nucleotide Sequences of Displayed Peptides from Selected Monoclonal Phages (Inverse Consensus Sequences)

| Monoclonal Isolate | Peptide Sequence | Nucleotide Sequence |
|---|---|---|
| Inverse of Ph.D.-C7C-6 | MTKHLPS (SEQ ID NO: 9) | 5'-ATGACCAAACATCTGCCGAGC-3' (SEQ ID NO: 13) |
| Inverse of Ph.D.-C7C-7 | KTKKMGS (SEQ ID NO: 10) | 5'-AAAACCAAAAAAATGGGCAGC-3' (SEQ ID NO: 14) |
| Inverse of Ph.D.-C7C-9 | LGMKTTK (SEQ ID NO: 11) | 5'-CTGGGCATGAAAACCACCAAA-3' (SEQ ID NO: 15) |
| Inverse of Ph.D.-12-2 Ph.D.-12.-7 | GEDMVGNGHILK (SEQ ID NO: 12) | 5'-GGCGAAGATATGGTGGGCAACGGCCATA TTCTGAAA-3' (SEQ ID NO: 16) |

Most antibody-based solutions require either special storage conditions or, if lyophilized, reconstitution prior to administration; both of which diminish their utility under the kinds of remote and austere conditions that animal envenomation often occurs. Disclosed herein are peptide solutions that do not require special storage conditions.

In some embodiments, the peptides disclosed herein are stable at room temperature. In some embodiment, the peptides disclosed herein are stable at −80° C. In some embodiment, the peptides disclosed herein are stable at −80° C. In some embodiment, the peptides disclosed herein are stable at −70° C. In some embodiment, the peptides disclosed herein are stable at −60° C. In some embodiment, the peptides disclosed herein are stable at −50° C. In some embodiment, the peptides disclosed herein are stable at −40° C. In some embodiment, the peptides disclosed herein are stable at −30° C. In some embodiment, the peptides disclosed herein are stable at −20° C. In some embodiment, the peptides disclosed herein are stable at −10° C. In some embodiment, the peptides disclosed herein are stable at 0° C. In some embodiment, the peptides disclosed herein are stable at 10° C. In some embodiment, the peptides disclosed herein are stable at 20° C. In some embodiment, the peptides disclosed herein are stable at 30° C. In some embodiment, the peptides disclosed herein are stable at 40° C. In some embodiment, the peptides disclosed herein are stable at 50° C.

In one embodiment, the peptides disclosed herein comprise $PLA_2$ consensus peptides of the Western Cottonmouth snake. In a specific embodiment, venom from *A. p. leucostoma* snake was synthesized and screened by Ph.D.™-7, Ph.D.™-12, and Ph.D™-C7C phage display peptide libraries (New England BIOLABS®, Inc., Ipswich, Mass.). As described below, four unique monoclonal anti-$PLA_2$ phage clones which inhibited 35 to 60% of $PLA_2$ activity were selected.

c. Peptide Production

The M13 phage of one embodiment of the present disclosure can be inexpensively and safely propagated in specialized *Escherichia coli* K12 ER2738, which lacks common pathogenicity-related sequences. The resulting product can be purified more efficiently than antiserums.

The development of a particular antivenom formulation using the methods of the present disclosure is fast and simple enough to allow for customization to a particular need. One cycle of selection will take one week and a whole selection of candidate phages can be completed in approximately 2 to 6 months. Because synthesis of phage-based antidotes according to the present disclosure can utilize a nonpathogenic strain of *E. coli*, rather than requiring large or dangerous animals, the risks and burdens of maintaining such animals in a laboratory setting is avoided.

Peptide target design based on the consensus $PLA_2$ protein sequence in Western Cottonmouth venom thus provides a useful target for the affinity partitioning of phage display libraries. Peptide affinity assay using ELISA test and venom component ($PLA_2$ or protease) activity assay can be used to assess the validity of a display phage-based antivenom. An in silico approach to epitope targeting allows for ubiquitous targeting of protein families or super families, such as targeting $PLA_2$ in specific genera. The $PLA_2$ active region has a ~95% homology in *A. piscovorus* species. Random targeting of the target sequence gives rise to several binders expressing variable motifs that inhibit activity through different mechanisms, creating a stronger suppression effect. When expanded to venomous snakes common to North America, the homology of the current $PLA_2$ construct drops to as low as 56% in Western Diamondback Rattlesnake (*Crotalus atrox*). Redefining the target sequence to include homologous regions of the five most common venomous snakes in North America, the consensus can be raised to 97%. Further defining the target peptide to mimic conserved active and metal-binding sites in these homologous regions of peptide families thus provides an improved method of developing a universal antivenom. Their structural and functional relationship has become generally known. This knowledge, however, has not facilitated the development of universal antivenoms, due to the limitations of antibody-based anti-venom production methods. The phage-display methods of the present disclosure, however, can be implemented using the results of similarity searches using a BlastX algorithm. Venom sequences can then be categorized and used as target peptides for the development of phage-based anti-venom. As such, universal antivenoms can be developed that target consensus sequences of any reptiles, arachnids, sea jellies, or other venomous animals.

In some embodiments, disclosed herein are methods of producing a peptide disclosed herein. The methods comprise identifying a peptide target based on a consensus $PLA_2$ protein sequence in Western Cottonmouth venom to provide a target for phage display panning; redefining a target sequence to include homologous regions of at least five common venomous snakes in North America; and redefining a target peptide to mimic homologous regions of peptide families through targeting conserved active sites.

Exemplary North American snakes include, but are not limited to Eastern Diamondback Rattlesnake (*Crotalus adamanteus*); Western Diamondback Rattlesnake (*Crotalus atrox*); Western coral snake (*Micruroides euryxanthus*); Eastern coral snakes (*Micrurus fulvius*) coral snake; copperhead (*Agkistrodon contortrix*); cottonmouth; yellowbelly sea snake (*Pelamis platura*); timber rattlesnake (*Crotalus horridus*); Mojave rattler (*Crotalus scutulatus*); and black rattlesnake (*Sistrurus catenatus*).

d. Polynucleotides

In certain aspects, provided herein are polynucleotides comprising a nucleotide sequence encoding an peptide described herein that bind to conserved snake venom components, and neutralize venom toxicity. In some embodiments, disclosed herein are poly Disclosed herein are polynucleotides comprising a sequence selected from the groups consisting of SEQ ID NOs: 5-8. In one embodiment, disclosed herein is a polynucleotides comprising SEQ ID NO:5. In one embodiment, disclosed herein is a polynucleotides comprising SEQ ID NO:6. In one embodiment, disclosed herein is a polynucleotides comprising SEQ ID NO:7. In one embodiment, disclosed herein is a polynucleotides comprising SEQ ID NO:8.

Also disclosed herein are polynucleotides comprising a sequence selected from the groups consisting of SEQ ID NOs: 13-16. In one embodiment, disclosed herein is a polynucleotides comprising SEQ ID NO:13. In one embodiment, disclosed herein is a polynucleotides comprising SEQ ID NO:14. In one embodiment, disclosed herein is a polynucleotides comprising SEQ ID NO:15. In one embodiment, disclosed herein is a polynucleotides comprising SEQ ID NO:16

Provided herein are polynucleotides comprising nucleotide sequences encoding any of the peptides provided herein, as well as vectors comprising such polynucleotide sequences, e.g., expression vectors for their efficient expression in host cells, e.g., M13 bacteriophages.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a peptide described herein is isolated or purified.

Also provided herein are polynucleotides encoding a peptide comprising SEQ ID NOs: 1-4 and SEQ ID NOs: 13-16 that are optimized, e.g., by codon/RNA optimization, replacement with heterologous signal sequences, and elimination of mRNA instability elements. Methods to generate optimized nucleic acids encoding a peptide disclosed herein for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of a peptide disclosed herein by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of peptide disclosed herein encoded by polynucleotides that have not been optimized.

In certain embodiments, an optimized polynucleotide sequence encoding a peptide disclosed herein can hybridize to an antisense (e.g., complementary) polynucleotide of an unoptimized polynucleotide sequence encoding a peptide described herein.

The polynucleotides can be obtained, and the nucleotide sequence of the polynucleotides determined, by any method known in the art. Nucleotide sequences encoding peptides described herein can be determined using methods well known in the art, i.e., nucleotide codons known to encode particular amino acids are assembled in such a way to generate a nucleic acid that encodes the peptide. Such a polynucleotide encoding a peptide disclosed herein can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the peptide, annealing and ligating of those oligonucleotides, and then amplification of the ligated oligonucleotides by PCR.

Alternatively, a polynucleotide encoding a peptide described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the peptide of interest. The amplified nucleic acids can be cloned into vectors for expression in host cells and for further cloning.

A nucleic acid encoding a peptide disclosed herein can be chemically synthesized or obtained from a suitable source by PCR amplification using synthetic primers hybridizable to the 3' and 5' ends of the sequence or by cloning using an oligonucleotide probe specific for the particular gene sequence to identify, e.g., a cDNA clone from a cDNA library that encodes a peptide disclosed herein. Amplified nucleic acids generated by PCR can then be cloned into replicable cloning vectors using any method well known in the art.

DNA encoding peptides described herein can be readily isolated and sequenced using conventional procedures (e.g., by using oligonucleotide probes)

Also provided are polynucleotides that hybridize under high stringency, intermediate or lower stringency hybridization conditions to polynucleotides that encode a peptide described herein. Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1× SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3 e. Cells and Vectors

In certain aspects, provided herein are cells (e.g., host cells) expressing (e.g., recombinantly) peptides described herein (or an antigen-binding fragment thereof) which specifically bind to $PLA_2$ and related polynucleotides and expression vectors. Provided herein are vectors (e.g., expression vectors) comprising polynucleotides comprising nucleotide sequences encoding peptides disclosed herein or a fragment for recombinant expression in host cells. Also provided herein are host cells comprising such vectors for recombinantly expressing peptides described herein. In a particular aspect, provided herein are methods for producing a peptide described herein, comprising expressing such peptide from a host cell.

In some embodiments, M13 phages express peptides disclosed herein. M13 phages are utilized as delivery vehicles to transport various binding motifs to targets. In some embodiments, genetic modification to phage tail proteins allows for the expression of unique peptides of variable sequences, length, and composition. Expressed peptides can bind to specific epitopes, forming the basis of a high throughput system for identifying binding partners. In some embodiments, M13 phages express peptides selected from the group consisting of SEQ ID NOs:1-4.

In some embodiments, M13 phages express peptides comprising SEQ ID NO:1. In some embodiments, M13 phages express peptides comprising SEQ ID NO:2. In some embodiments, M13 phages express peptides comprising SEQ ID NO:3. In some embodiments, M13 phages express peptides comprising SEQ ID NO:4.

In some embodiments, M13 phages express peptides comprising SEQ ID NO:13. In some embodiments, M13 phages express peptides comprising SEQ ID NO:14. In some embodiments, M13 phages express peptides comprising SEQ ID NO:15. In some embodiments, M13 phages express peptides comprising SEQ ID NO:16.

In some embodiments, M13 phages have a long plasma half-life (t ½=4.5 hours).

M13 phages disclosed herein are stable in the pH range 3-11. In some embodiments, the pH of the M13 phage is 3. In some embodiments, the pH of the M13 phage is 4. In some embodiments, the pH of the M13 phage is 5 In some embodiments, the pH of the M13 phage is 6. In some embodiments, the pH of the M13 phage is 7. In some embodiments, the pH of the M13 phage is 7.4. In some embodiments, the pH of the M13 phage is 8. In some embodiments, the pH of the M13 phage is 9. In some embodiments, the pH of the M13 phage is 10. In some embodiments, the pH of the M13 phage is 11.

The M13 phages disclosed herein are also resistant to temperatures below 80° C.

The M13 phages disclosed herein have a half-life of over 6 months in culture media at room temperature without any special storage conditions.

Once a polynucleotide encoding a peptide described herein has been obtained, the vector for the production of the peptide molecule can be produced by recombinant DNA technology using techniques well known in the art.

Thus, methods for preparing a protein by expressing a polynucleotide containing a protein encoding nucleotide sequence are described herein. Methods which are well known to those skilled in the art can be used to construct expression vectors containing protein coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a protein described herein, operably linked to a promoter.

An expression vector can be transferred to a cell (e.g., host cell) by conventional techniques and the resulting cells can then be cultured by conventional techniques to produce a protein described herein. Thus, provided herein are host cells containing a polynucleotide encoding a protein described herein or fragments thereof, operably linked to a promoter for expression of such sequences in the host cell.

A variety of host-expression vector systems can be utilized to express peptides described herein Such host-expression systems represent vehicles by which the coding sequences of interest can be produced and subsequently purified, but also represent cells which can, when transformed or transfected with the appropriate nucleotide coding sequences, express a peptide described herein in situ. These include but are not limited to microorganisms such as bacteria (e.g., *E. coli* and *B. subtilis*) transformed with recombinant bacteriophage DNA, plasmid DNA or cosmid DNA expression vectors containing peptide coding sequences; yeast (e.g., *Saccharomyces Pichia*) transformed with recombinant yeast expression vectors containing peptide coding sequences; insect cell systems infected with recombinant virus expression vectors (e.g., baculovirus) containing peptide coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing peptide coding sequences; or mammalian cell systems (e.g., COS (e.g., COS1 or COS), CHO, BHK, MDCK, HEK 293, NS0, PER.C6, VERO, CRL7030, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In some embodiments, the host cell is *Escherichia coli*. In one particular embodiment, the host cell is *Escherichia coli* K12 ER2738.

In some embodiments, cells for expressing peptides described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells).

In bacterial systems, a number of expression vectors can be used. For example, when a large quantity of such a peptide is to be produced, for the generation of pharmaceutical compositions of a peptide molecule, vectors which direct the expression of high levels of protein products that are readily purified can be desirable. Such vectors include, but are not limited to, the *E. coli* expression vector pUR278 (Ruether U & Mueller-Hill B (1983) EMBO J 2: 1791-1794), in which the peptide coding sequence can be ligated individually into the vector in frame with the lac Z coding region so that a fusion protein is produced; pN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST).

In an insect system, *Autographa californica* nuclear polyhedrosis virus (AcNPV), for example, can be used as a vector to express foreign genes. The virus grows in *Spodoptera frugiperda* cells. The peptide coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the peptide coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the peptide molecule in infected hosts (e.g., see Logan J & Shenk T (1984) PNAS 81(12): 3655-9). Specific initiation signals can also be required for efficient translation of inserted peptide coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells.

In a specific embodiment, the peptides described herein have reduced fucose content or no fucose content. Such peptides can be produced using techniques known one skilled in the art. For example, the peptides can be expressed in cells deficient or lacking the ability of to fucosylate. In a specific example, cell lines with a knockout of both alleles of α1,6-fucosyltransferase can be used to produce peptides with reduced fucose content. The Potelligent® system (Lonza) is an example of such a system that can be used to produce peptides with reduced fucose content.

For long-term, high-yield production of recombinant proteins, stable expression cells can be generated.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express a peptide described herein. Such engineered cell lines can be particularly useful in screening and evaluation of compositions that interact directly or indirectly with the peptide molecule.

A number of selection systems can be used, including but not limited to, the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes can be employed in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbere-Garapin F et al., (1981) J Mol Biol 150: 1-14, which are incorporated by reference herein in their entireties.

The expression levels of a peptide can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing peptide is amplifiable, increase in the level of inhibitor present in culture of host cell will increase the number of copies of the marker gene. Since the amplified region is associated with the peptide gene, production of the peptide will also increase (Crouse G F et al., (1983) Mol Cell Biol 3: 257-66).

Once a peptide described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the peptides described herein can be fused to heterologous polypeptide sequences described herein or otherwise known in the art to facilitate purification.

In specific embodiments, a peptide described herein is isolated or purified. Generally, an isolated peptide is one that is substantially free of other peptides with different antigenic specificities than the isolated peptide. For example, in a particular embodiment, a preparation of a peptide described herein is substantially free of cellular material and/or chemical precursors. The language "substantially free of cellular material" includes preparations of a peptide in which the peptide is separated from cellular components of the cells from which it is isolated or recombinantly produced. Thus, a peptide that is substantially free of cellular material includes preparations of a peptide having less than about 30%, 20%, 10%, 5%, 2%, 1%, 0.5%, or 0.1% (by dry weight) of heterologous protein (also referred to herein as a "contaminating protein") and/or variants of a peptide. When the peptide is recombinantly produced, it is also generally substantially free of culture medium, i.e., culture medium represents less than about 20%, 10%, 2%, 1%, 0.5%, or 0.1% of the volume of the protein preparation. When the peptide is produced by chemical synthesis, it is generally substantially free of chemical precursors or other chemicals, i.e., it is separated from chemical precursors or other chemicals which are involved in the synthesis of the protein. Accordingly, such preparations of the peptide have less than about 30%, 20%, 10%, or 5% (by dry weight) of chemical precursors or compounds other than the peptide of interest. In a specific embodiment, peptides described herein are isolated or purified.

f. Compositions and Pharmaceutical Compositions

Disclosed herein are compositions comprising peptides comprising a sequence selected from the groups consisting of SEQ ID NOs: 1-4 and SEQ ID NOs: 9-12. Also disclosed herein is a composition comprising a peptide comprising SEQ ID NO:1, SEQ ID NO:2, SEQ ID NO:3, SEQ ID NO:4, SEQ ID NO:9, SEQ ID NO:10, SEQ ID NO:11, and SEQ ID NO:12, or any combination thereof.

In one embodiment, disclosed herein is a composition comprising a peptide comprising SEQ ID NO:1. In one embodiment, disclosed herein is a composition comprising a peptide comprising SEQ ID NO:2. In one embodiment, disclosed herein is a composition comprising a peptide comprising SEQ ID NO:3. In one embodiment, disclosed herein is a composition comprising a peptide comprising SEQ ID NO:4. In one embodiment, disclosed herein is a composition comprising a peptide comprising SEQ ID NO:9. In one embodiment, disclosed herein is a composition comprising a peptide comprising SEQ ID NO:10. In one embodiment, disclosed herein is a composition comprising a peptide comprising SEQ ID NO:11. In one embodiment, disclosed herein is a composition comprising a peptide comprising SEQ ID NO:12.

In some embodiments, the peptides disclosed herein are formulated with a range of alternate delivery systems such as nanoparticles. In some embodiments, a composition comprising a nanoparticle and a peptide disclosed herein are provided. In some embodiments, the present disclosure provides an aqueous liposome nanoparticle composition comprising an aqueous dispersion of liposome nanoparticles and a peptide disclosed herein. In some embodiments, the nanoparticles encapsulate a peptide disclosed herein. In some embodiments, a peptide disclosed herein is added to a pre-formed liposome composition. In other embodiments, a peptide disclosed herein is incorporated in the liposomes during the formation of the liposomes.

Also provided herein are compositions comprising a peptide described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise a peptide described herein, and optionally one or more additional prophylactic or therapeutic agents, in a pharmaceutically acceptable carrier. In a specific embodiment, pharmaceutical compositions comprise an effective amount of a peptide described herein, and optionally one or more additional prophylactic of therapeutic agents, in a pharmaceutically acceptable carrier. In some embodiments, the peptide is the only active ingredient included in the pharmaceutical composition. Pharmaceutical compositions described herein can be useful in strongly binding to conserved snake venom components and neutralizing venom toxicity.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition can be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Preparations for parenteral administration of composition comprising a peptide disclosed herein include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising a composition comprising a peptide disclosed herein are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

A composition comprising a peptide disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the peptide alone or in combination with other pharmaceutically acceptable excipients can also be administered.

Transdermal patches, including iontophoretic and electrophoretic devices, are well known to those of skill in the art, and can be used to administer a peptide disclosed herein. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, each of which is incorporated by reference in its entirety.

In certain embodiments, a pharmaceutical composition comprising a peptide described herein is a lyophilized powder, which can be reconstituted for administration as solutions, emulsions and other mixtures. It may also be reconstituted and formulated as solids or gels. The lyophilized powder is prepared by dissolving a peptide described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The peptides described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, each of which is incorporated by reference in its entirety.

The compositions to be used for in vivo administration can be sterile. This is readily accomplished by filtration through, e.g., sterile filtration membranes.

g. Uses and Methods

The present disclosure relates to an improved method for generating a universal antivenom. According to the improved method, phage display techniques offer an alternative tool for the selection of phage-expressed peptides which can bind with high specificity and affinity to many different venom targets.

The novel method disclosed herein results in an antivenom that has lower production cost, shorter synthesis time, and fewer adverse reactions than any antivenom production method known in the prior art. Additionally, antivenom produced by the present method is stable in long-term storage in liquid form at ambient temperatures, a feature previously thought to be impossible for antivenom.

h. Detection & Diagnostic Uses

Their amino acid sequences, inhibitory effect, and cross-species reactivity were evaluated.

This novel approach removes the need for helper phage, vector recloning, and additional single chain fragment variable (scFv) antibody purification steps, in addition to the universal antivenom.

A peptide disclosed herein or composition comprising a peptide disclosed herein can be used to assay venomous levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label a peptide disclosed herein or composition comprising a peptide.

Assaying for the detectable level of venom is intended to include qualitatively or quantitatively measuring or estimating the level of venom in a first biological sample either directly (e.g., by determining or estimating absolute venom level) or relatively (e.g., by comparing to the disease associated venom level in a second biological sample). Venom level in the first biological sample can be measured or estimated and compared to a standard venom level, the standard being taken from a second biological sample obtained from an individual not exposed to a venomous bite or being determined by averaging levels from a population of individuals not exposed to venom. As will be appreciated in the art, once the "standard" venom level is known, it can be used repeatedly as a standard for comparison.

As used herein, the term "biological sample" refers to any biological sample obtained from a subject, cell line, tissue, or other source of cells potentially expressing peptides disclosed herein. Methods for obtaining tissue biopsies and body fluids from animals (e.g., humans) are well known in the art. Biological samples include peripheral mononuclear blood cells.

A peptide disclosed herein or composition comprising a peptide disclosed herein can be used for prognostic, diagnostic, monitoring, and screening applications, including in vitro and in vivo applications well known and standard to the skilled artisan and based on the present description. Prognostic, diagnostic, monitoring, and screening assays and kits for in vitro assessment and evaluation of immune system status and/or immune response may be utilized to predict, diagnose and monitor to evaluate patient samples including those known to have or suspected of being exposed to a venomous bite or with regard to an anticipated or desired immune system response or antigen response.

In one embodiment, a peptide disclosed herein or composition comprising a peptide disclosed herein can be used in immunohistochemistry of biopsy samples.

In another embodiment, a peptide disclosed herein or composition comprising a peptide disclosed herein can be used to detect levels of PLA$_2$. A peptide disclosed herein or composition comprising a peptide disclosed herein may carry a detectable or functional label. When fluorescence labels are used, currently available microscopy and fluorescence-activated cell sorter analysis (FACS) or combination of both methods procedures known in the art may be utilized to identify and to quantitate the specific binding members. A peptide disclosed herein or composition comprising a peptide disclosed herein may carry a fluorescence label. Exemplary fluorescence labels include, for example, reactive and conjugated probes e.g. Aminocoumarin, Fluorescein and Texas red, Alexa Fluor dyes, Cy dyes and DyLight dyes. A peptide disclosed herein or composition comprising a peptide disclosed herein may carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of a peptide disclosed herein or composition comprising a peptide disclosed herein to $PLA_2$. In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with a peptide disclosed herein or composition comprising a peptide disclosed herein under conditions that allow for the formation of a complex between a peptide disclosed herein or composition comprising a peptide disclosed herein and $PLA_2$. Any complexes formed between a peptide disclosed herein or composition comprising a peptide disclosed herein and $PLA_2$ are detected and compared in the sample and the control. A peptide disclosed herein or composition comprising a peptide disclosed herein can also be used to purify $PLA_2$ via immunoaffinity purification.

Also included herein is an assay system which may be prepared in the form of a test kit for the quantitative analysis of the extent of the presence of, for instance, $PLA_2$. The system or test kit may comprise a labeled component, e.g., a labeled antibody, and one or more additional immunochemical reagents. See, e.g., (h) below for more on kits.

i. Therapeutic Uses and Methods

In some embodiments, the peptides bind to snake venom and neutralize venom toxicity. In some embodiments, the peptides bind to $PLA_2$ and neutralize venom toxicity. M13 phage can also be cleared from the body without adverse reactions, which can occur with antibody-based antiserum therapy (e.g., serum sickness). The methods of the present disclosure can be implemented to quickly and easily custom-design an antivenom that is universal to any particular subset of venomous animals, and stable under conditions that antibody-based therapies cannot tolerate.

A peptide disclosed herein or composition comprising a peptide disclosed herein can be delivered to a subject by a variety of routes. In some embodiments, the peptide or composition is delivered via parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray.

The amount of a peptide disclosed herein or composition comprising a peptide disclosed herein which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For passive immunization with a peptide disclosed herein, the dosage ranges from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. In some embodiments, the dosage administered to the patient is about 1 mg/kg to about 20 mg/kg of the patient's body weight.

An exemplary treatment regime entails administration once or with repeated doses. Intervals between single dosages can be hourly, daily, weekly, monthly, every 3 months, every 6 months or yearly.

j. Kits

In some embodiments, provided herein are kits comprising one or more peptides disclosed herein. In a specific embodiment, provided herein is a pharmaceutical pack or kit comprising one or more containers filled with one or more of the ingredients of the proteins, nucleic acids, or pharmaceutical compositions described herein, such as one or more proteins provided herein. In some embodiments, the kits contain a pharmaceutical composition described herein and any prophylactic or therapeutic agent, such as those described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

In some embodiments, provided herein is a diagnostic kit for identifying the type and severity of a venomous animal bite. In some embodiments, the kit comprises (a) a plurality of peptides, each peptide targeting a sequence unique to one of a plurality of animal venoms; (b) a plurality of label molecules, each label molecule conjugated to a corresponding one of the plurality of peptides; and (c) an assay configured to detect the label molecules and thereby display peptides that are bound to their respective targets.

In some embodiments, the present disclosure also provides a diagnostic kit for identifying the type and severity of a venomous animal bite. In some embodiments, the kit comprises a plurality of peptides. In some embodiments, the kit comprises a plurality of label molecules. In some embodiments, each peptide in the kit targets a sequence of the venom of a unique species. In some embodiments, one or more peptides in the kit targets a sequence unique to the venom of the same species.

In some embodiments, the sample tested in the kit is blood. In a specific embodiment, the sample tested in the kit is human blood. In some embodiments, the sample is isolated and contacted with one or more peptides in the kit. In some embodiments, the peptides in the kit are labeled.

In some embodiments, the kit also includes an assay configured to detect the label molecules and thereby display the peptides that are bound to their respective targets in the blood. In some embodiments, the kit can therefore detect which peptides have bound to targets, and the extent of the binding, thereby identifying what animal species venom is found in the blood and the severity of the bite.

Also provided herein are kits that can be used in the above methods. In one embodiment, a kit comprises a protein described herein, preferably a purified protein, in one or more containers. In one embodiment, a kit comprises a composition comprising a protein described herein in one or more containers. In a specific embodiment, kits described herein contain a substantially isolated protein as a control. In another specific embodiment, the kits described herein further comprise a control antibody which does not react with the universal venom antigen. In another specific embodiment, kits described herein contain one or more elements for detecting the binding of a protein or composition comprising a protein to a universal venom antigen (e.g., the protein can be conjugated to a detectable substrate such as a fluorescent compound, an enzymatic substrate, a radioactive compound or a luminescent compound, or an antibody which recognizes the protein disclosed herein can be conjugated to a detectable substrate). In specific embodiments, a kit provided herein can include a recombinantly produced or chemically synthesized protein disclosed herein. The universal venom antigen provided in the kit can also be attached to a solid support. In a more specific embodiment, the detecting means of the above described kit includes a solid support to which a universal venom antigen is attached. Such a kit can also include a non-attached reporter-labeled anti-human antibody or anti-mouse/rat antibody. In this embodiment, binding of the protein to the venom can be detected by binding of the said reporter-labeled antibody.

The following examples are offered by way of illustration and not by way of limitation.

EXAMPLES

Example 1

Western Cottonmouth (*A. p. leucostoma*) $PLA_2$ protein sequence information was retrieved and the sequence was screened for its active sites and homology to other $PLA_2$ proteins using the Basic Local Alignment Search Tool (BLAST) (Altschul, S. F., Gish, W., Miller, W., Myers, E. W., Lipman, D. J. (1990) Basic Local Alignment Search Tool. J. Mol. Bioi. 215:403-410). A conserved 57 amino acid consensus peptide was designed, and compared using BLAST to determine sequence homology between related five major venomous snake species in North America, with a similarity of ≥95%.

$PLA_2$ 3D Crystal Structure analysis was performed to view solvent accessibility of targeted consensus sequence amino acids (IPPA—www.RCSB.org Protein Data Bank notation).

This 57 amino acid consensus peptide was synthesized as the target peptide using the 9-fluorenylmethoxycarbonyl/tert-butyl solid-phase peptide synthesis method with ~98% purity. It was then precipitated as the acetate salt form through custom peptide synthesis services for panning purposes.

An enhanced panning method was utilized instead of the standard 96-well plate panning system described by the Ph.D. Phage Display Library manual. The glass surface of capillary tubes was crosslinked to the target peptide to present the mimicked active site to phage display libraries. A crosslinking procedure using a cleavable crosslinker, Sulfo-LC-SPDP [sulfosuccinimidyl 6-(3'-(2-pyridyldithio)propionamido)hexanoate] bound the target peptide to an aminosilylated (3-Aminopropyltriethoxysilane) glass capillary tube. A 10 t volume Microcaps capillary tube (21-170° F.) was washed with high-performance liquid chromatography grade acetone, and treated with aminosilane reagent. The silylated glass capillary tube was modified directly with 10 mM Sulfo-LC-SPDP. The glass-crosslinking capillary tube was incubated for 1 hour at room temperature (RT), and then rinsed twice with Coupling Buffer. The SPDP-modified capillary tube was filled with the target $PLA_2$ peptide at 10 mg/ml in water, and incubated overnight at 4° C. to complete the crosslinking reaction. The advantages of using a 10 µl capillary tube phage display selection system becomes clear as it minimizes the required volumes of hazardous chemicals, concentrated peptide, and the phage library needed per panning procedure (next section).

Phages were then panned against target proteins using the modified panning methodology derived from the instruction manual of the Ph.D. Phage Display Libraries. Namely, tubing circuits containing the peptide-crosslinked 10 µl Microcaps capillary tubes were made using a Multichannel Heidolph peristaltic pump and Marprene (0.5 mm bore 1.6 mm wall) tubing. The small 10 J·tl volume of the Microcaps capillary tubes plus accompanying tubing (~250 µl) only requires a minimal volume of diluted phage library (2.5 µl library diluted in 247.5 µl blocking buffer for $10^{11}$ phage isolates panned). The circuit was coated with blocking buffer, then phage library dilutions were routed through the system to select for strongly binding phage to the cross-linked peptides on the capillary tube surface. Phages bound to capillary tube were eluted using either Elution Buffer [25 mM Dithiothreitol (DTT), pH 8.5] for Ph.D.™-7 and Ph.D.™-12 libraries or Acidic Elution Buffer (0.2 M Glycine-HCl (pH 2.2), 1 mg/ml BSA) for Ph.D.™-C7C phage library isolates after incubating the tubing circuit at 37° C. or room temperature (RT) for 30 minutes, depending on the library used. Eluted phages were captured and neutralized using 1M Tris-HCl (pH 9.1).

Phages were harvested using a polyethylene glycol (PEG) precipitation method. Amplified phage stocks were mixed with ⅙ total volume 20% PEG-8000/2.5 M NaCl solution, then allowed to precipitate in 50 ml Oakridge tubes at 4° C. overnight. Chilled phages were then pelleted through centrifugation (Avanti JXN-30, Beckman Coulter, Brea, Calif.) at 12,000 rpm at 4° C. for 20 minutes. Resuspended phages were collected after the final centrifuge run and resuspended in PBS, pH 7.5. Collected phages were tittered on isopropyl-P-Dthiogalactoside/5-Bromo-4-chloro-3-indolyl-P-D-galactoside (50 mM IPTG I 40 mM XGAL) media using manufacturer's manual. Secondary panned polyclonal phage solutions were used for initial $PLA_2$ inhibition testing, and monoclonal phage isolates were individually picked from soft agar titer plates and amplified.

Analysis of PLAz activity was conducted using the EnzChek® PLAz Assay Kit (Thermo Fisher Scientific, Waltham, Mass.). Individual phage clones were standardized to 1.0x 1012 PFU/ml and diluted in log steps. Diluted phages were incubated with 4.88 µg/ml Western Cottonmouth venom for 30 minutes at RT. Fluorescence emission spectra (excitation at 485 nm, emission at 528 nm) was measured for 20 minutes at 1.0 minute intervals to monitor the reaction. $PLA_2$ activity was determined by comparing the phage inhibited venom to uninhibited venom controls.

FIG. 1 shows the crystal structure of $PLA_2$ isolated from Western Cottonmouth (*A. p. leucostoma*) venom shown in a space filling model. Residues have been identified using yellow and red circles, denoting catalytic active sites and metal binding amino acids respectively. These solvent exposed residues are possible sites of phage binding. Bound phages in this area could disrupt enzymatic activity of the protein and result in limiting damage from venom activity.

Initial polyclonal phage mixtures from secondary panned phage against $PLA_2$ consensus peptide were incubated with Western Cottonmouth venom (4.88 µg/ml) for 30 minutes. After incubation, the enzymatic activity of $PLA_2$ was measured using a Phospholipase A2 assay. Fluorescence was measured in triplicates of venom only, and 1:4 and 1:1 dilutions. These results are shown in FIG. 2. The amount of phage present affected the intensity of the measurable fluorescence. The monoclonal phage isolates from this polyclonal phage mixtures are listed in Table 1.

Table 1 tabulates monoclonal phage isolates, by nucleotide and peptide sequence. Phage DNA was isolated from infected cells, and sequenced. The resulting chromatograph was interpreted to determine the nucleotide sequence, which was then translated to a peptide sequence. The nucleotide sequences of isolates Ph.D.-12-2 and Ph.D.-12-5 are the same, indicating multiple isolates of this phage were isolated. One of the repeated phage was removed from further studies to avoid repetition.

TABLE 2

Nucleotide Sequences and Corresponding Peptide Sequences for Selected Monoclonal Phage Binding Motifs
Peptide Sequences and Nucleotide Sequences of Displayed Peptides from Selected Monoclonal Phages

| Monoclonal Isolate | Peptide Sequence | Nucleotide Sequence |
|---|---|---|
| Ph.D.-C7C-6 | SPLHKTM (SEQ ID NO: 1) | 5'-TCGCCGTTGCATAAGACTATG-3' (SEQ ID NO: 5) |
| Ph.D.-C7C-7 | SGMKKTK (SEQ ID NO: 2) | 5'-TCGGGGATGAAGAAGACGAAG-3' (SEQ ID NO: 6) |
| Ph.D.-C7C-9 | KTTKMGL (SEQ ID NO: 3) | 5'-AAGACGACGAAGATGGGGTTG-3' (SEQ ID NO: 7) |
| Ph.D.-12-2 Ph.D.-12.-7 | KLIHGNGVMDEG (SEQ ID NO: 4) | 5'-AAGCTTATTCATGGTAATGG TGTTATGGATGAGGGG-3' (SEQ ID NO: 8) |

Figure 3:
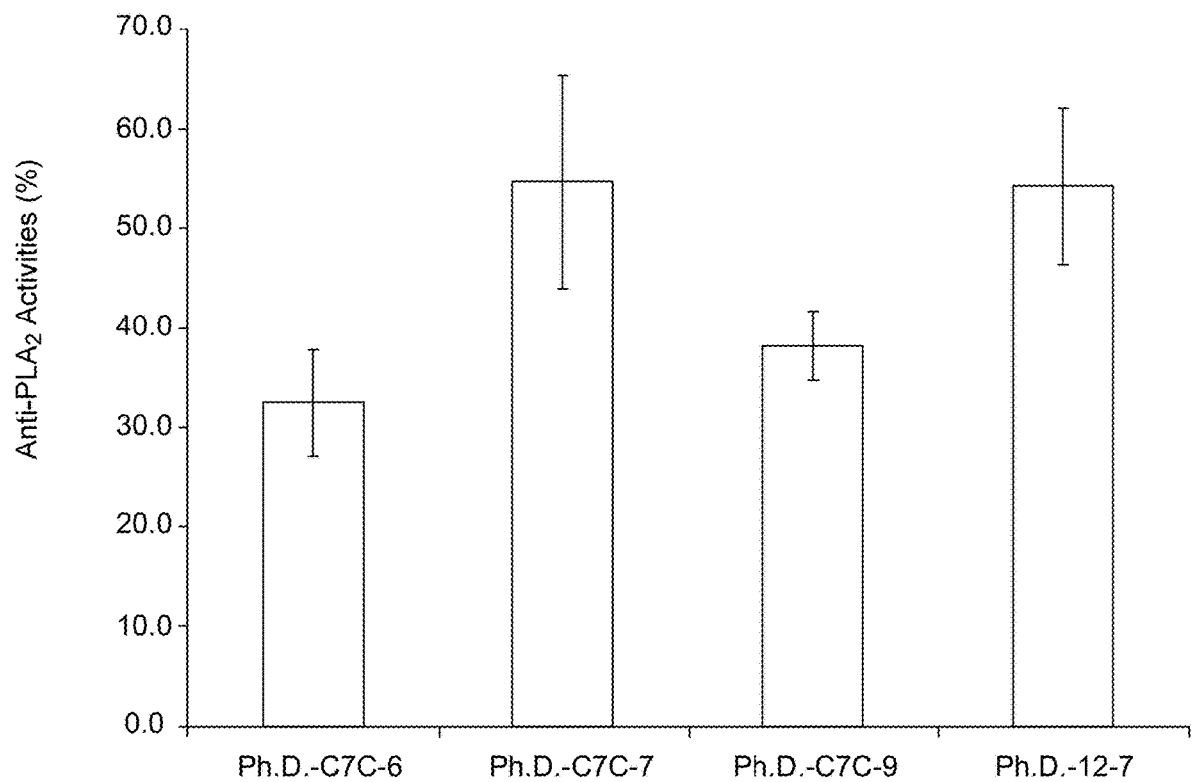
FIG. 3 is a bar graph showing Inhibition of PLA$_2$ activity using phage clones isolated from phage display libraries.

FIG. 3 shows inhibition of PLA$_2$ activity using phage clones isolated from phage display libraries isolated. Single phage isolates were incubated with Western Cottonmouth venom (4.88 μg/ml) for 30 minutes before PLA$_2$ substrate was added. The reaction was monitored, with the time point corresponding to 10 minutes displayed in FIG. 3. The individual isolates reduced PLA$_2$ activity between 35%-60%.

As seen in FIG. 2, the amount of phages present impacts the intensity of measurable fluorescence. The 1:4 dilutions do not statistically reduce the fluorescence intensity of the assay, but when a 1:1 dilution of phage to venom reduction in fluorescent signal is concentration dependent; demonstrating that higher concentrations of phage would further reduce enzymatic activity of PLA$_2$. The inhibitory action of monoclonal phage isolates was assayed in the same manner as the polyclonal mixtures. Monoclonal phage isolates inhibited PLA$_2$ to a greater extent than the polyclonal mixture at the same dilution rate (FIG. 3). Individual isolates reduced PLA$_2$ activity to 35 to 60% of uninhibited activity. PLA$_2$ inhibition can be increased by targeting unique binding epitopes of the active region, due to the multitude of possible binding motifs present on the individual phage isolates. Utilization of phage cocktails thus would have synergistic effects.

Figure 4:
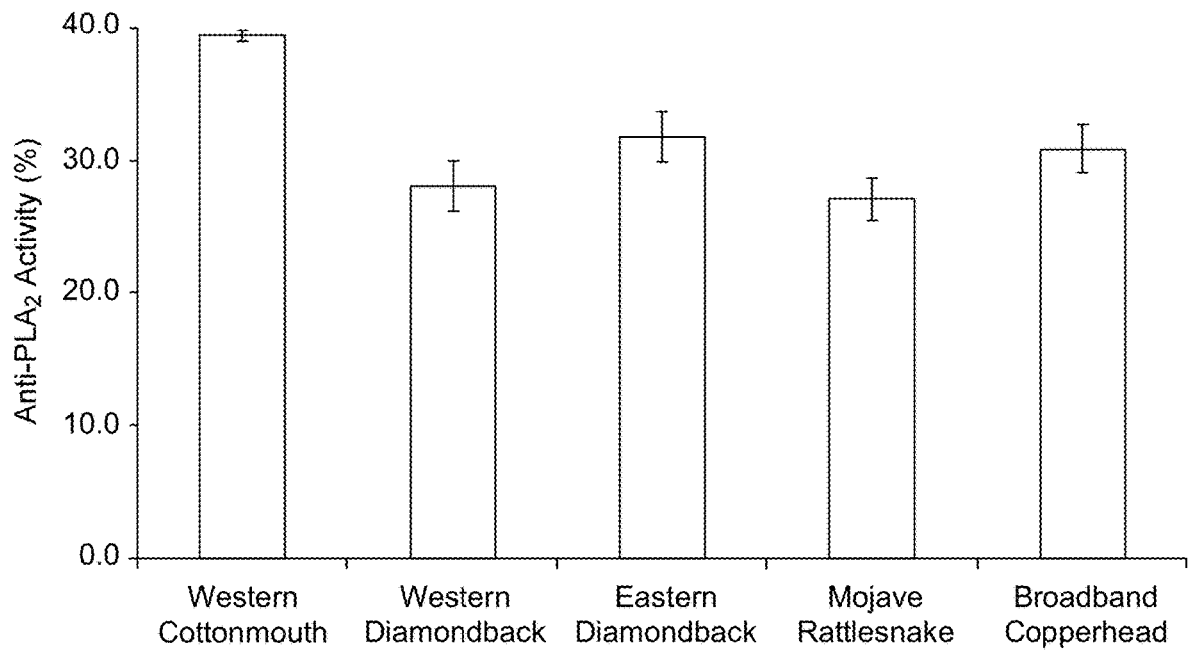
FIG. 4 is a bar graph showing cross-species anti-PLA$_2$ activities of Ph.D.-12-7 phages against five major snake venoms in the U.S. One of the selected phage clones, Ph.D.-12-7 showed anti-PLA$_2$ activities across all major North American crotalid venoms.
Figure 5:
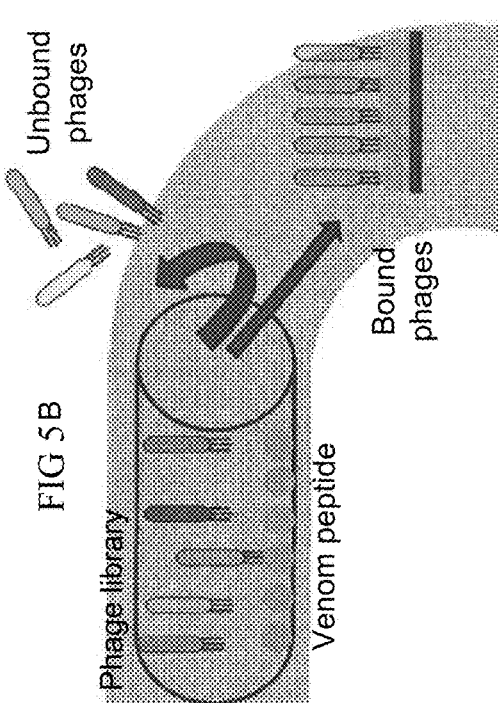
FIG. 5A-5D illustrate the steps of the method for developing a universal antivenom from a variety of phage display systems.
Figure 5:
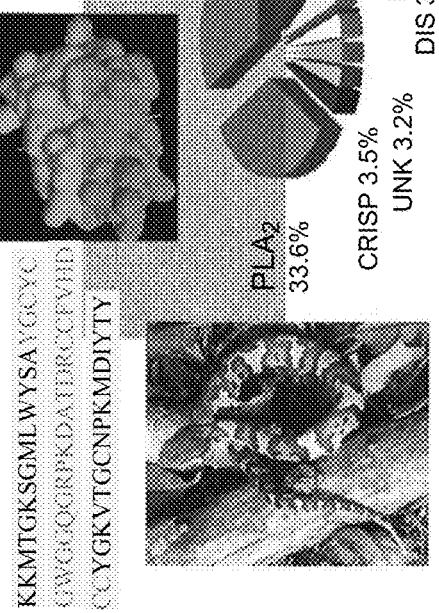
Figure 5:
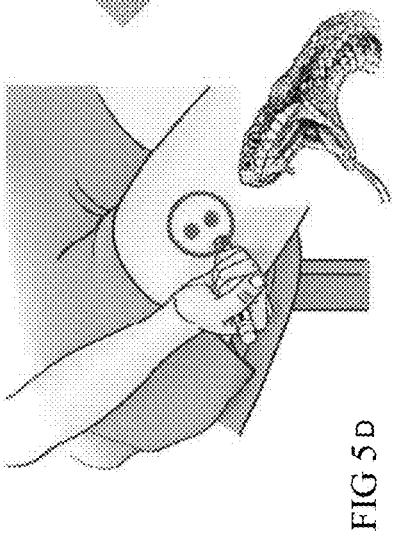

FIG. 4 shows cross-species anti-PLA$_2$ activity of one of the selected phage clones, Ph.D.-12-7 against five major North America snakes. Originally consensus peptide for panning target was designed with ~95% homology of all major North American crotalid PLA$_2$. This cross-species reactivity of the selected phage clone is the best evidence for the potential development of a universal antivenom using phage display technique.

Example 2

A subject is contacted by animal venom through e.g., a snake bite. In response, a therapeutically effective amount of a multi-species antivenom composition comprising an M13-phage-expressed peptide described herein is administered. Treatment dosage of the composition is titrated to optimize safety and efficacy. Administration of the composition comprising a phage-expressed peptide described herein neutralizes venom toxicity by binding to conserved PLA$_2$. Afterwards, the M13 phage is cleared from the body without adverse reactions. If necessary, further administrations of a therapeutically effective amount of a multi-species antivenom composition comprising an M13-phage-expressed peptide described herein is administered.

Example 3

A subject is contacted by animal venom through e.g., a snake bite. In response, a therapeutically effective amount of a multi-species antivenom composition comprising an M13-phage-expressed peptide described herein is administered. Treatment dosage of the composition is titrated to optimize safety and efficacy. Administration of the composition comprising a phage-expressed peptide described herein neutralizes venom toxicity. Afterwards, the M13 phage is cleared from the body without adverse reactions. If necessary, further administrations of a therapeutically effective amount of a multi-species antivenom composition comprising an M13-phage-expressed peptide described herein is administered.

What is claimed is:

1. A multi-species antivenom composition comprising a phage-expressed peptide that binds to a target common to more than one animal venoms; and a pharmaceutically acceptable carrier, wherein the phage-expressed peptide is selected from the group consisting of SEQ ID NO:1, SEQ ID NO:2, SEQ ID NO:3, SEQ ID NO:4, SEQ ID NO: 9, SEQ ID NO: 10, SEQ ID NO: 11, SEQ ID NO: 12, and any combination thereof.

2. The composition of claim 1, wherein the phage-expressed peptide is about 7 to about 12 amino acids in length; and wherein the target is a metal, a carbohydrate, a protein, or any combination thereof.

3. The composition of claim 1, wherein the peptide is linear.

4. The composition of claim 1, wherein the peptide is circular.

5. The composition of claim 1, wherein the target is phospholipase $A_2$ ($PLA_2$).

6. A phage-expressed peptide that binds to a target in one or more animal venoms, wherein the peptide is selected from the group consisting of SEQ ID NO:1, SEQ ID NO:2, SEQ ID NO:3, SEQ ID NO:4, of SEQ ID NO: 9, SEQ ID NO: 10, SEQ ID NO: 11, SEQ ID NO: 12, and any combinations thereof.

7. The phage-expressed peptide of claim 6, wherein the target is phospholipase $A_2$.

8. The phage-expressed peptide of claim 6, wherein the phage-expressed peptide is expressed by a M13 phage.

9. A diagnostic kit comprising the composition of claim 1.

* * * * *